United States Patent [19]

Kulprathipanja et al.

[11] Patent Number: 4,924,027

[45] Date of Patent: May 8, 1990

[54] SEPARATION OF SALTS OF CITRIC ACID FROM FERMENTATION BROTH WITH A WEAKLY BASIC ANIONIC EXCHANGE RESIN ADSORBENT

[75] Inventors: Santi Kulprathipanja, Inverness; Scott A. Strong, Des Plaines, both of Ill.

[73] Assignee: UOP, Des Plaines, Ill.

[21] Appl. No.: 275,827

[22] Filed: Nov. 25, 1988

Related U.S. Application Data

[63] Continuation-in-part of Ser. No. 121,830, Nov. 16, 1987, Pat. No. 4,851,573, which is a continuation-in-part of Ser. No. 943,219, Dec. 18, 1986, Pat. No. 4,720,579.

[51] Int. Cl.$^5$ ............................................. C07C 51/42
[52] U.S. Cl. ..................................................... 562/580
[58] Field of Search ........................................ 562/580

[56] References Cited

U.S. PATENT DOCUMENTS

| 2,664,441 | 12/1953 | Owens et al. | 260/527 |
|---|---|---|---|
| 4,031,038 | 6/1977 | Grinstead et al. | 260/2.2 R |
| 4,098,867 | 7/1978 | Grinstead et al. | 423/24 |
| 4,323,702 | 4/1982 | Kawabata et al. | 562/485 |
| 4,720,579 | 1/1988 | Kulprathipanja | 562/580 |

FOREIGN PATENT DOCUMENTS

| 151470 | 5/1984 | European Pat. Off. |
|---|---|---|
| 868926 | 6/1957 | United Kingdom . |
| 2064526 | 6/1981 | United Kingdom . |

OTHER PUBLICATIONS

Johnson, J., Sci. Food Agric., vol. 33(3) pp. 287-293, Handbook of Chemistry & Physics, 53rd Ed. 1972-3 CRC Press.

*Primary Examiner*—Paul J. Killos
*Attorney, Agent, or Firm*—Thomas K. McBride; John F. Spears, Jr.; Jack H. Hall

[57] ABSTRACT

Salts of citric acid are separated from a fermentation broth by a two-step process utilizing an adsorbent comprising a water-insoluble, macroreticular gel, weakly basic, anionic exchange resin possessing tertiary amine functional groups or pyridine functional groups, said anionic exchange resin comprising a crosslinked acrylic or styrene resin matrix and a desorbent comprising water or dilute sulfuric acid. The pH of the feed, a fermentation broth, containing citric acid, is adjusted and maintained below the first ionization constant ($pKa_1$) of citric acid to maintain selectivity in the first step wherein citric acid is adsorbed onto the adsorbent. Then, citric acid is converted to a salt by a reaction with an aqueous alkaline liquid solution and is eluted immediately at the void volume in the alkaline solution.

9 Claims, 1 Drawing Sheet

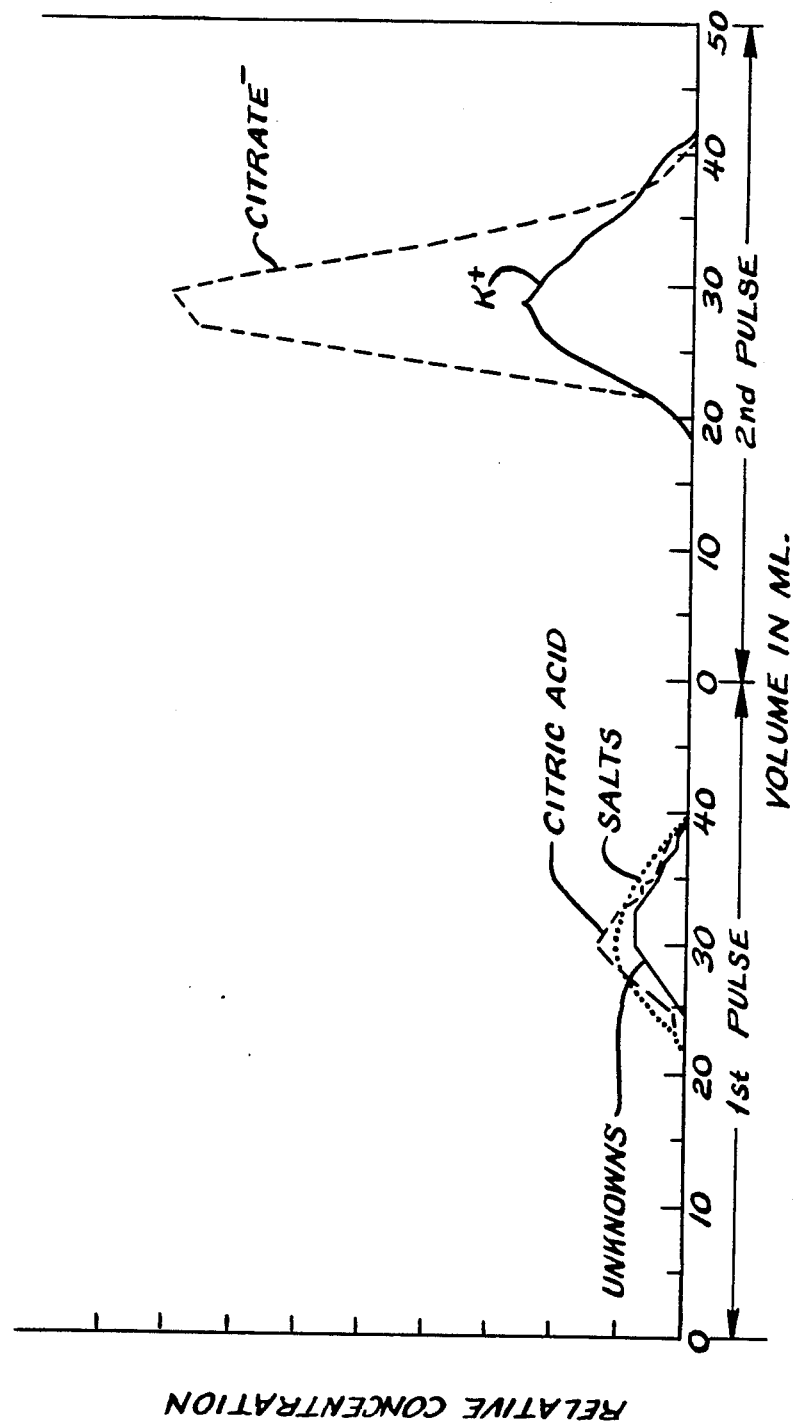

SEPARATION OF SALTS OF CITRIC ACID FROM FERMENTATION BROTH WITH A WEAKLY BASIC ANIONIC EXCHANGE RESIN ADSORBENT

CROSS-REFERENCE TO RELATED APPLICATIONS

This is a continuation in part of Ser. No. 121,830, filed Nov. 16, 1987, now U.S. Pat. No. 4,851,573 which is a continuation-in-part of Ser. No. 943,219, filed Dec. 18, 1986, now U.S. Pat. No. 4,720,579.

FIELD OF THE INVENTION

The field of art to which this invention pertains is the solid bed adsorptive separation of citric acid from fermetation broths containing citric acid, carbohydrates, amino acids, protein and salts. More specifically, the invention relates to a process for separating citric acid in salt form which process employs an adsorbent comprising basic anionic exchange resin adsorbents, which selectively adsorb citric acid from a fermentation mixture containing said citrates.

BACKGROUND OF THE INVENTION

Citric acid is used as a food acidulant, and in pharmaceutical, industrial and detergent formulations. The increased popularity of liquid detergents formulated with citric acid has been primarily responsible for growth of worldwide production of citric acid to about 700 million pounds per year which is expected to continue in the future. Furthermore, in many applications, such as in food, beverages, pharmaceuticals and liquid detergents, the salts of citric acid, e.g., sodium-, potassium- and ammonium-citrate are used.

Citric acid is produced by a submerged culture fermentation process which employs molasses as feed and the microorganism, *Aspergillus Niger*. The fermentation product will contain carbohydrates, amino acids, proteins and salts as well as citric acid, which must be separated from the fermentation broth.

There are two technologies currently employed for the separation of citric acid from fermentation broths containing the same. The first involves calcium salt precipitation of citric acid. The resulting calcium citrate is acidified with sulfuric acid. In the second process, citric acid is extracted from the fermentation broth with a mixture of trilauryl-amine, n-octanol and a $C_{10}$ or $C_{11}$ isoparaffin. Citric acid is reextracted from the solvent phase into water with the addition of heat. Both techniques, however, are complex, expensive and they generate a substantial amount of waste for disposal.

The patent literature has suggested a possible third method for separating citric acid from the fermentation broth, which involves membrane filtration to remove raw materials or high molecular weight impurities and then adsorption of contaminants onto a nonionic resin based on polystyrene or polyacrylic resins and collection of the citric acid in the rejected phase or raffinate and crystallization of the citric acid after concentrating the solution, or by precipitating the citric acid as the calcium salts then acidifying with $H_2SO_4$, separating the $CaSO_4$ and contacting cation-and anion-exchangers. This method, disclosed in European Published Application No. 151,470, Aug. 14, 1985, is also a rather complex and lengthy method for separating the citric acid.

U.S. Pat. No. 4,323,702, corresponding to British Patent No. 2,064,526A discloses that citric acid may be adsorbed from aqueous solutions thereof onto a porous, crosslinked pyridine group-containing polymer made from an ethylenically unsaturated monomer, e.g., a vinyl pyridine monomer. However, the polymer is used as a free base and the acid is desorbed by an organic solvent, such as an alcohol or a ketone. Furthermore, there is not teaching or suggestion to separate citric acid from a fermentation broth containing other organic materials.

The establishment of pH below the pk value in an adsorbent separation of citric acid from other acids is disclosed in U.S. Pat. No. 2,664,441, but there is no suggestion of or rationale for the application thereof to the instant separation of citric acid from mixtures thereof with non-acidic components.

In Kulprathipanja Patent 4,720,579, referred to above, citric acid is separated from a fermentation broth by using an adsorbent comprising a neutral, non-iogenic, macroreticular, water-insoluble, crosslinked styrene-poly(vinyl)benzene and a desorbent comprising water and, optionally, acetone with the water. The pH of the feed is adjusted and maintained below the first ionization constant ($pKa_1$) of citric acid to maintain selectivity. However, separation of citric acid by the process disclosed therein has the drawback that it is an extractive process and requires a substantial volume of desorbent liquid and amount of time to recover the citric acid from the adsorbent. One aspect of that invention was in the discovery that complete separation of citric acid from salts and carbohydrates with neutral resins is only achieved by adjusting and maintaining the pH of the feed solution lower than the first ionizaton constant ($pKa_1$) of citric acid (3.13).

The degree to which the pH must be lowered to maintain adequate selectivity appears to be interdependent on the concentration of citric acid in the feed mixture; i.e., the pH is invesely dependent on the concentration. As concentrations are decreased below 13% to very low concentrations, the pH may be near the $pKa_1$ of citric acid of 3.13; at 13%, the pH may range from 0.9 to 1.7; however, at 40% citric acid feed concentration, the pH mut be lowered to at least about 1.2 or lower. At higher concentrations, the pH must be even lower; for example, at 50% citric acid, the pH must be at or below 1.0. Another aspect of that invention was the discovery that the temperature of separation can be reduced by the addition of cetone, or other low molecular weight ketone, to the adsorbent; the higher temperatures associated with adsorbent breakdown can thus be avoided.

The invention disclosed in my parent application Ser. No. 121,830, filed Nov. 16, 1987, also relates to a process for separating citric acid from a feed mixture comprising a fermentation broth employing water-insoluble, macroreticular or gel, weakly basic anionic exchange resin possessing tertiary amine functional groups or pyridine functional groups having a crosslinked acrylic or styrene resin matrix.

Accordingly, it is an object of the present invention to separate citric acid from the impurities in a fermentation broth in a simple and economic process by adsorbing citric acid on an adsorbent and recovering the citric acid in the form of its salts. Succinctly stated, the citric acid is adsorbed selectively by the adsorbent, and the impurities are removed by elution with a weak desorbent, such as water, the adsorbed citric acid is converted to its salt by reaction with an aqueous alkaline solution, and the salt is spontaneously eluted by the aqueous solution.

SUMMARY OF THE INVENTION

This invention relates to a process for adsorbing citric acid from a fermentation broth onto a weakly basic, macroreticular or gel type, water-insoluble, anionic exchange resin matrix possessing tertiary amine or pyridine functional groups, reacting the adsorbed citric acid with an aqueous alkaline solution, e.g., potassium, sodium or ammonium hydroxide, to convert the citric acid to the salt thereof, which is immediately eluted with the aqueous solutions such as KOH, NaOH and NHHD 4OH. The resin matrix is either acrylic or styrene, crosslinked with divinylbenzene. The salts are formed from citric acid after the acid has been adsorbed on the weakly basic resin adsorbent (to the exclusion of other components and impurities in the feed), but before being desorbed. Elution of the citric acid in salt form is advantageous in that many commercial applications involve the direct addition of citrates to formulations such as those previously mentioned and, therefore, an additional chemical reaction is not required. Also, since the recovery of the citrate is rejective, i.e., in the raffinate, the cycle time is lower than for an extractive process, such as disclosed in U.S. Pat. No. 4,720,579, and therefore, the process is more economical.

In a specific modification, the invention relates to a process for separating citric acid from a fermentation broth feed mixture, containing citric acid and impurities, comprising contacting said mixture with a water-insoluble, macroreticular or gel, weakly basic anionic exchange resin possessing tertiary amine or pyridine functional groups, said weakly basic anionic exchange resin having a crosslinked acrylic or styrene resin matrix at adsorption conditions selected to selectively adsorb said citric acid, contacting said adsorbent with a weak desorbent liquid such as water or very dilute sulfuric acid, for a period of time to elute the nonadsorbed components of said feed and any that are less strongly adsorbed that citric acid, reacting the adsorbed citric acid with an aqueous alkaline solution whereby said citric acid is converted to a salt and eluted at the void volume.

Other aspects of the invention encompass details of feed mixtures, adsorbents, desorbents and operating conditions which are hereinafter disclosed.

BRIEF DESCRIPTION OF THE DRAWINGS

FIG. 1 is the plot of the pulse test in Example I using a weakly basic anionic exchange resin having a tertiary amine functionality in a crosslinked polystyrene resin matrix to separate citric acid from a feed containing 13% citric acid at a pH of 2.4, in two steps, first, adsorbing said citric acid on said exchange resin, contacting said adsorbent with water to elute salts and unknown impurities, converting the adsorbed citric acid to potassium citrate by reacting with potassium hydroxide (KOH), which is immediately eluted at the void volume by the aqueous solution without addition of further desorbent.

DESCRIPTION OF THE INVENTION

At the outset, the definitions of various terms used throughout the specification will be useful in making clear the operation, objects and advantages of our process.

A "feed mixture" is a mixture containing one or more extract components and one or more raffinate components to be separated by our process. The term "feed stream" indicates a stream of a feed mixture which passes to the adsorbent used in the process.

An "extract component" is a compound or type of compound that is more selectively adsorbed by the adsorbent while a "raffinate component" is a compound or type of compound that is less selectively adsorbed. In this process, a salt of citric acid is raffinate component and the process includes removal of proteins, amino acids, salts and carbohydrates, and other raffinate components before converting the citric acid, which is adsorbed by the adsorbent, to a salt which then immediately elutes as a second raffinate component. By contrast, in the prior process of the parent application, citric acid was recovered in the extract by completing the desorption step with water or dilute sulfuric acid.

The term "desorbent material" shall mean generally a material capable of desorbing an extract component, although in the instant process, there is no adsorbed species remaining to be desorbed following the elution of the potassium citrate with the KOH solution at the void volume.

The term "raffinate stream" or "raffinate output stream" means a stream through which a raffinate component is removed from the adsorbent. The composition of the raffinate stream can vary from essentially 100% desorbent material to essentially 100% raffinate components. At least a portion of the raffinate stream from the separation process are passed to separation means, typically fractionators, where at least a portion of desorbent material is separated to produce a raffinate product. The term "raffinate product" means product produced by the process containing, a raffinate component in higher concentrations than those found in the feed stream.

The term "selective pore volume" of the adsorbent is defined as the volume of the adsorbent which selectively adsorbs an extract component from the feed mixture, e.g., the citric acid present in the original feed material. The term "nonselective void volume" of the adsorbent is the volume of the adsorbent which does not selectively retain an extract component from the feed mixture. This volume includes the cavities of the adsorbent which contain no adsorptive sites and the intersitial void spaces between adsorbent particles. The selective pore volume and the nonselective void volume are generally expressed in volumetric quantities.

One feed material contemplated in this invention is the fermentation product obtained from the submerged culture fermentation of molasses by the microorganism, *Aspergillus Niger*. The fermentation product will have a composition exemplified by the following:

TABLE 1

| Feed Composition | Amount |
|---|---|
| Citric acid | 12.9% |
| Salts | 6,000 ppm |
| Carbohydrates (sugars) | 1% |
| Others (proteins and amino acids) | 2% |

The salts will include K, Na, Ca, Mg and Fe. The carbohydrates are sugars including glucose, xylose, mannose, oligosaccharides of DP2 and DP3 plus as many as 12 or more unidentified saccharides. The composition of the feedstock may vary from that given above and still be used in the invention. For example, the above feed may be concentrated to 40% citric acid by evaporating water therefrom to obtain a preferred feed material for this process having the following composition.

TABLE 2

| Feed Composition | Amount |
|---|---|
| Citric Acid | 40% (wt.) |
| Salts ($K^+$, $Na^+$, $Ca^{++}$, $Mg^{++}$, $Fe^{+++}$) | 1.5% |
| Carbohydrates (Sugars) | 4% |
| Others ($SO_4^=$, $Cl^-$, $PO_4^\equiv$, $NO_3^-$, proteins and amino acids) | 5% |
| | 49.5% |

However, juices, such as citrus fruit juices, are not acceptable or contemplated because other materials contained therein will be adsorbed at the same time rather than citric acid alone. Johnson, *J. Sci. Food Agric.*, Vol 33(3) pp 287-93.

I disclosed in the parent application that the separation of citric acid can be enhanced significantly by adjusting the pH of the feed to a level below the first ionization constant of citric acid. The first ionization constant ($pKa_1$) of citric acid is 3.13, *Handbook of Chemistry & Physics*, 53rd Edition, 1972-3, CRC Press, and therefore, the pH of the citric acid feed should be below 3.13. When the pH for a 40% concentrated solution of citric acid is 3.5 or greater, for example, as in FIGS. 7A and 7B and Example II of copending Ser. No. 121,830, citric acid "breaks through" (is eluted) with the salts and carbohydrates at the beginning of the cycle, indicating that most of the citric acid is not adsorbed. In contrast, no "break through" of citric acid is observed when the pH is below 2.2, for example as in FIGS. 11A and 11B and Example IV of Ser. No. 121,830. We believe that the explanation given in the parent, Ser. No. 943,219, case may be correct, and is incorporated herein in its entirety by reference. Briefly stated, as demonstrated in FIGS. 1 and 2 therein, the concentration of nonionized citric acid (the adsorbed species) is increased, while reducing the citrate species ($H_2CA^{-1}$, $HCA^{-2}$ and $CA^{-3}$) in the solution, as the pH is decreased. This is an important facet of the first step of the instant process for separating the salts of citric acid. Before conversion, it is essential to maintain the pH low, as taught in the parent applications, to prevent "break through" of citric acid and consequent loss of citric acid in the first raffinate. Then, after treatment with an aqueous alkaline solution and conversion of the acid to the salt, all the citrate "breaks through" and is recovered in the second raffinate. In this stage, the high pH is advantgeous for recovering citrate because it promotes the "break through" at the void volume.

The aqueous alkaline solution may be any alkali metal, alkaline earth metal or ammonium hydroxide. Potassium hydroxide is used to demonstrate our invention.

Desorbent materials used in various prior art adsorptive separation processes vary depending upon such factors as the type of operation employed. In the swing bed system, which is contemplated here as the process of choice, the selectively adsorbed feed component is held on the adsorbent during the first desorption step, during which the non-adsorbed impurities are eluted at the void volume. To avoid loss of citric acid in this stage, a weak desorbent is essential. Therefore, water is preferred, but dilute sulfuric acid (0.01 to 1.0N) is also suitable. In the second stage of the process, the adsorbent holding the adsorbed citric acid is contacted with an aqueous alkaline solution, e.g., sodium, potassium of ammonium hydroxide, which reacts with the citric acid in situ and converts it to the citrate. Because the citrates are not adsorbed by the adsorbent, the citrates will be eluted immediately, at the void volume, with the alkaline solution. Therefore, it is esssential that the so-called "desorbent" selected for this process be weak enough that citric acid will not be desorbed or eluted in the first raffinate or that the desorption step be terminated before any substantial amounts of citric acid are actually desorbed. The aqueous alkaline solutions are compatible with the water desorbent of the first stage, although after the citrates are eluted, none of the feed material remains on the adsorbent, so no desorption step is necessary. The adsorbent is ready to be contacted by new feed material for a subsequent separation. The process may be made continuous by alternating the feed, water and hyroxide solution to two or more columns and installing appropriate valving.

The prior art has also recognized that certain characteristics of adsorbents are highly desirable, if not absolutely necessary, to the successful operation of a selective adsorption process. Such characteristics are equally important to this process. Among such characteristics are: (1) adsorptive capacity for some volume of an extract component per volume of adsorbent; (2) the selective adsorption of an extract component with respect to a raffinate component and the desorbent material; and (3) sufficiently fast rates of adsorption and desorption of an extract component to and from the adsorbent. Capacity of the adsorbent for adsorbing a specific volume of an extract component is, of course, a necessity; without such capacity the adsorbent is useless for adsorptive separation. Furthermore, the higher the adsorbent's capacity for an extract component the better is the adsorbent. Increased capacity of a particular adsorbent makes it possible to reduce the amount of adsorbent needed to separate an extract component of known concentration contained in a particular charge rate of feed mixture. A reduction in the amount of adsorbent required for a specific adsorptive separation reduces the cost of the separation process. It is important that the good initial capacity of the adsorbent be maintained during actual use in the separation process over some economically desirable life. The second necessary adsorbent characteristic is the ability of the adsorbent to separate components of the feed; or, in other words, that the adsorbent possess adsorptive selectivity, ($\beta$), for one component as compared to another component. Relative selectivity is expressed for one feed component as compared to another. The selectivity, ($\beta$), as used throughout this specification is defined as the ratio of the two components of the adsorbed phase over the ratio of the same two components in the unadsorbed phase at equilibrium conditions. Relative selectivity is shown as Equation 1 below:

$$\text{Selectivity} = (\beta) = \frac{\text{vol. percent } C/\text{vol. percent } D_A}{\text{vol. percent } C/\text{vol. percent } D_U} \quad \text{Equation 1}$$

where C and D are two components of the feed represented in volume percent and the subscripts A and U represent the adsorbed and unadsorbed phases respectively. The equilibrium conditions were determined when the feed passing over a bed of adsorbent did not change composition after contacting the bed of adsorbent. In other words, there was no net transfer of material occurring between the unadsorbed and adsorbed phases. Where selectivity of two components approaches 1.0, there is no preferential adsorption of one component by the adsorbent with respect to the other; they are both adsorbed (or nonadsorbed) to about the same degree with respect to each other. As the ($\beta$) becomes less than or greater than 1.0 there is a preferential adsorption by the adsorbent for one component with respect to the other. When comparing the selectivity by the adsorbent of one component C over component D, a ($\beta$) larger than 1.0 indicates preferential adsorption of component C within the adsorbent. A ($\beta$) less than 1.0 would indicate that component D is preferentially adsorbed leaving an unadsorbed phase richer in component C and an adsorbed phase richer in component D. While separation of an extract component from a raffinate component is theoretically possible when the selectivity of the adsorbent for the extract component with respect to the raffinate component is greater than 1, it is preferred that such selectivity approach a value of 2. Like relative volatility, the higher the selectivity, the easier the separation is to perform. Higher selectivities permit a smaller amount of adsorbent to be used.

A dynamic testing apparatus is employed to test various adsorbents with a particular feed mixture and desorbent material to measure the adsorbent characteristics of adsorptive capacity, selectivity and exchange rate. The apparatus consists of an adsorbent chamber comprising a straight or helical column of approximately 70 cc volume having inlet and outlet portions at opposite ends of the chamber. The chamber is contained within a temperature control means and, in addition, pressure control equipment is used to operate the chamber at a constant predetermined pressure. Quantitative and qualitative analytical equipment such as refractometers, polarimeters and chromatographs can be attached to the outlet line of the chamber and used to detect quantitatively or determine qualitatively one or more components in the effluent stream leaving the adsorbent chamber. A pulse test, performed using this apparatus and the following geneal procedure, is used to determine selectivities and other data for various adsorbent systems. The adsorbent is filled to equilibrium with a particular desorbent material by passing the desorbent material through the adsorbent chamber. At a convenient time, a pule of feed containing known concentrations of a tracer and of a particular extract component or of a raffinate component or both, all diluted in desorbent, is injected for a duration of several minutes. Desorbent flow is resumed, and the tracer and the raffinate component or the extract component (or both) are eluted as in a liquid-solid chromatographic operation. The effluent can be analyzed onstream or, alternatively, effluent samples can be collected periodically and later analyzed separately by analytical equipment and traces of the envelopes of corresponding component peaks developed.

From information derived from the test adsorbent, performance can be in terms of void volume, retention volume for an extract or a raffinate component, selectivity for one component with respect to the other, and the rate of desorption of an extract component by the desorbent. The retention volume of an extract or a raffinate component may be characterized by the distance between the center of the peak envelope of an extract or a raffinate component and the peak envelope of the tracer component or some other known reference pont. It is expressed in terms of the volume in cubic centimeters of desorbent pumped during this time interval represented by the distance between the peak envelopes. Selectivity, ($\beta$), for an extract component with respect to a raffinate component may be characterized by the ratio of the distance between the center of the extract component peak envelope and the tracer peak envelope (or other reference point) to the corresponding distance between the center of the raffinate component peak envelope and the tracer peak envelope.

Adsorbents to be used in the process of this invention will comprise weakly basic anion exchange resins possessing tertiary amine or pyridine functionality in a crosslinked polymeric matrix, e.g., acrylic or styrene. They are especially suitable when produced in bead form, have a high degree of uniform polymeric porosity, exhibit chemical and physical stability and good resistance to attrition (not common to macroreticulr resins).

Adsorbents such as just described are manufactured by the Rohm and Haas Company, and sold under the trade name "Amberlite." The types of Amberlite polymers known to be effective for use by this invention are referred to in Rohm and Haas Company literature as Amberlite adsorbents XE-275 (IRA-35), IRA-68, and described in the literature as "insoluble in all common solvents and having open structure for effective adsorption and desorption of large molecules without loss of capacity due to organic fouling." Also suitable are AG3-X4A and AG4-X4 manufactured by Bio Rad and comparable resins sold by Dow Chemical Co., such as Dowex 66, and Dow experimental resins made in accordance with U.S. Pat. Nos. 4,031,038 and 4,098,867.

The various types of polymeric adsorbents of these classes available, will differ somewhat in physical properties such as porosity volume percent, skeletal density and nominal mesh sizes, and perhaps more so in surface area, average pore diameter and dipole moment. The preferred adsorbents will have a surface area of 10-2000 square meters per gram and preferably from 100-1000 $m^2/g$. Specific properties of the materials listed above can be found in company literature and technical brochures, such as those in the following Table 3 which are incorporated herein by reference. Others of the general class are also available.

TABLE 3

| Adsorbent | Matrix Type | Reference to Company Literature |
|---|---|---|
| AG3-4A (Bio Rad) | Polystyrene | Chromatography Electrophoresis Immunochemistry Molecular Biology - HPLC - Price List M April 1987 (Bio-Rad) |
| AG4-X4 | Acrylic | Chromatography Electrophoresis Immunochemistry Molecular Biology - HPLC - Price List M April 1987 (Bio-Rad) |
| Dow Experimental Resins | Polystyrene | U.S. Pat. Nos. 4,031,038 and 4,098,867 |
| Dowex 66 | Polystyrene | Material Safety Data Sheet Printed 2/17/87 (Dow Chemical USA) |
| IRA-35 (XE-275) | Acrylic | Amberlite Ion Exchange Resins (XE-275) Rohm & Haas Co. 1975 |
| IRA-68 | Acrylic | Amberlite Ion Exchange Resins - Amberlite IRA-68 Rohm & Haas Co., April 1977 |

Applications for Amberlite polymeric adsorbents suggested in the Rohm and Haas Company literature include decolorizing pulp mill bleaching effluent, decolorizing dyes wastes and removing pesticides from waste effluent. There is, of course, no hint in the literature of our surprising discovery of the effectiveness of Amberlite polymeric adsorbents in the separation of salts of citric acid from *Aspergillus Niger* fermentatin broths.

The adsorbent may be employed in the form of a dense compact fixed bed which is alternatively contacted with the feed mixture and desorbent materials. In the simplest embodiment of the invention, the adsorbent is employed in the form of a single static bed in which case the process is only semicontinuous. In another embodiment a set of two or more static beds may be employed in fixed bed contacting with appropriate valving so that the feed mixture is passed through one or more adsorbent beds while the desorbent materials can be passed through one or more of the other beds in the set. The flow of feed mixture and desorbent materials may be either up or down through the desorbent. Any of the conventional apparatus employed in static bed fluid-solid contacting may be used.

Although both liquid and vapor phase operations can be used in many adsorptive separation processes, liquid-phase operation is preferred for this process because of the lower temperature requirements and because of the higher yields of extract product that can be obtained with liquid-phase operation over those obtained with vapor-phase operation. Adsorption conditions will include a temperature range of from about 20° C. to about 200° c. with about 50° C. to about 90° C. being more preferred and a pressure range of from about atmospheric to about 500 psig (3450 kPa gauge) being preferred to ensure liquid phase. Desorption conditions will include the same range of temperatures and pressures as used for adsorption.

The following examples are presented to illustrate the selectivity relationship that makes the process of our invention possible. The examples are not intended to unduly restrict the scope of claims attached hereto.

EXAMPLE

A pulse test using the procedure and apparatus described above was run at a temperature of 65° C., using water as desorbent and a weakly basic anionic exchange resin possessing a crosslinked polystyrene matrix (Dowex 66) as adsorbent with the fermentation fed mixture shown in Table 1, containing about 13% citric acid. The pH was 2.4 during the dsorption step, i.e., below the first ionization constant, $pKa_1 = 3.13$, of citric acid.

In the first part of this pulse test (which is identical to Example II and FIG. 7C of parent application, Ser. No. 121,830), a first desorbent material, water, eluted the non-adsorbed salts and unknowns with a small amount of the citric acid, which had been adsorbed, breaking through. A 1N solution of KOH was then passed through the column to convert the adsorbed citric acid to the potassium salt thereof. After 20 ml of KOH had been fed to the column (at 1.28 ml/min), the bulk of citric acid was eluted at the void volume as sodium citrate. In FIG. 1 the first pulse, i.e., the first 40 ml of desorbent, water, injected into the column, resulted in elution, at the void volume, of salts, unknowns and some citric acid. During the second pulse, during which KOH is injected, the citric acid is converted to the potassium salt and eluted immediately, i.e., at the void volume.

What is claimed is:

1. A process for separating citric acid from a fermentation broth feed mixture, containing citric acid and impurities, comprising contacting said mixture with a water-insoluble, macroreticular or gel, weakly basic anionic exchange resin possessng tertiary amine or pyridine functional groups, said weakly basic anionic exchange resin having a crosslinked acrylic or styrene resin matrix at adsorption conditions selected to selectively adsorb said citric acid, contacting said adsorbent with a weak desorbent liquid for a period of time to elute the non-adsorbed components of said feed, reacting the adsorbed citric acid with an aqueous alkaline solution whereby said citric acid is converted to a salt and eluted with said aqueous alkaline solution.

2. The process of claim 1 further characterized in that said weak desorbent liquid is water.

3. The process of claim 1 further characterized in that said adsorption conditions include a temperature within the range of from about 20° to about 200° C. and a pressure within the range of from about atmospheric to about 500 psig (3450 kPa gauge).

4. The process of claim 1 further characterized in that the pH of said feed mixture is lower than the first ionization constant ($pKa_1$) of citric acid.

5. The process of claim 1 further characterized in that said adsorbent has a tertiary amine functional group and said matrix is a crosslinked acrylic or styrene resin.

6. The process of claim 1 further characterized in that said aqueous alkaline solution comprises a solution selected from the group consisting of sodium hydroxide, potassium hydroxide and ammonium hydroxide.

7. The process of claim 1 further characterized in that said aqueous alkaline solution consists of potassium hydroxide.

8. The process of claim 1 further characterized in that said adsorbent has a surface area of at least $10 m^2/g$.

9. The process of claim 1 wherein said fermentation broth comprises citric acid, carbohydrates, protein, amino acid and salts.

* * * * *